(12) United States Patent
Pacetti

(10) Patent No.: US 7,341,630 B1
(45) Date of Patent: Mar. 11, 2008

(54) STENT COATING SYSTEM

(75) Inventor: Stephen Dirk Pacetti, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 561 days.

(21) Appl. No.: 10/606,712

(22) Filed: Jun. 26, 2003

(51) Int. Cl.
*B05C 5/00* (2006.01)
*B05C 13/02* (2006.01)
*B05B 7/06* (2006.01)

(52) U.S. Cl. ............... 118/300; 118/313; 118/320; 118/500; 239/290; 239/418; 239/428

(58) Field of Classification Search ............... 118/300, 118/306, 317, DIG. 10, DIG. 11, 313; 239/421–425, 239/304–306, 290, 428, 418
See application file for complete search history.

(56) References Cited

U.S. PATENT DOCUMENTS

| | | | | |
|---|---|---|---|---|
| 2,373,595 A | 4/1945 | Peeps | | 299/140.1 |
| 3,049,439 A * | 8/1962 | Coffman | | 427/137 |
| 3,232,540 A * | 2/1966 | Cassanmagnago | | 239/416 |
| 3,848,807 A | 11/1974 | Partida | | 239/290 |
| 4,733,665 A | 3/1988 | Palmaz | | 128/343 |
| 4,743,252 A | 5/1988 | Martin et al. | | 623/1.44 |
| 4,800,882 A | 1/1989 | Gianturco | | 128/343 |
| 4,886,062 A | 12/1989 | Wiktor | | 128/343 |
| 4,967,606 A | 11/1990 | Wells et al. | | 73/864.18 |
| 5,015,505 A | 5/1991 | Cetnar | | 427/286 |
| 5,225,750 A | 7/1993 | Higuchi et al. | | 318/280 |
| 5,249,746 A * | 10/1993 | Kaneko et al. | | 239/296 |
| 5,368,560 A | 11/1994 | Rambo et al. | | 604/35 |
| 5,437,889 A | 8/1995 | Jones | | 427/185 |
| 5,464,650 A | 11/1995 | Berg et al. | | 427/2.3 |
| 5,511,726 A | 4/1996 | Greenspan et al. | | 239/102.2 |
| 5,527,337 A | 6/1996 | Stack et al. | | 606/198 |
| 5,700,286 A | 12/1997 | Tartaglia et al. | | 623/1 |
| 5,713,949 A | 2/1998 | Jayaraman | | 623/1 |
| 5,741,554 A | 4/1998 | Tisone | | 427/424 |
| 5,766,710 A | 6/1998 | Turnlund et al. | | 428/36.1 |
| 5,769,883 A | 6/1998 | Buscemi et al. | | 623/1 |
| 5,810,254 A * | 9/1998 | Kropfield | | 239/61 |
| 5,824,056 A | 10/1998 | Rosenberg | | 623/1 |
| 5,837,313 A | 11/1998 | Ding et al. | | 427/2.21 |
| 5,843,172 A | 12/1998 | Yan | | 623/1 |
| 5,869,127 A | 2/1999 | Zhong | | 427/2.12 |
| 5,873,904 A | 2/1999 | Ragheb et al. | | 623/1 |
| 5,980,972 A | 11/1999 | Ding | | 427/2.24 |

(Continued)

FOREIGN PATENT DOCUMENTS

JP     2003211063 A * 7/2003

(Continued)

OTHER PUBLICATIONS

English Translated Abstract of JP2003211063A.*

(Continued)

*Primary Examiner*—Yewebdar Tadesse
(74) *Attorney, Agent, or Firm*—Squire Sanders & Dempsey LLP

(57) ABSTRACT

A nozzle for use in a coating apparatus for the application of a solvent and polymer to a stent is provided.

13 Claims, 4 Drawing Sheets

U.S. PATENT DOCUMENTS

| | | | |
|---|---|---|---|
| 5,984,449 A | 11/1999 | Tajika et al. | 347/15 |
| 6,056,993 A | 5/2000 | Leidner et al. | 427/2.25 |
| 6,096,070 A | 8/2000 | Ragheb et al. | 623/1 |
| 6,121,027 A | 9/2000 | Clapper et al. | 435/180 |
| 6,132,809 A | 10/2000 | Hynes et al. | 427/421 |
| 6,143,370 A | 11/2000 | Panagiotou et al. | 427/422 |
| 6,209,621 B1 | 4/2001 | Treacy | 164/516 |
| 6,214,407 B1 | 4/2001 | Laube et al. | 427/2.24 |
| 6,224,675 B1 | 5/2001 | Prentice et al. | 118/669 |
| 6,395,326 B1 | 5/2002 | Castro et al. | 427/2.24 |
| 6,462,284 B1 | 10/2002 | Hashimoto | 174/260 |
| 6,491,666 B1 | 12/2002 | Santini, Jr. et al. | 604/191 |
| 6,503,954 B1 * | 1/2003 | Bhat et al. | 514/772.2 |
| 2003/0099765 A1 * | 5/2003 | Jayaraman | 427/2.24 |

FOREIGN PATENT DOCUMENTS

| | | |
|---|---|---|
| WO | WO 98/23228 | 6/1998 |

OTHER PUBLICATIONS

"Impulse Jetting: About Us," http://www.impulsejetting.com/about.html, printed Dec. 18, 2000; 1 page.

"Impulse Jetting: Our Technology," http://www.impulsejetting.com/tech1.html, printed Dec. 18, 2000; 1 page.

Trident, Inc., http://www.tridetintl.com/subbody.html, printed Sep. 18, 2003 (1 page).

World Precision Instruments, Inc., "Nanolite Injector," http://www.wpiinc.com/WPI_Web/Microinjection/Nanoliter_Injector.html, printed Sep. 18, 2003 (2 pages).

World Precision Instruments, Inc., "Pneumatic PicoPumps," http://www.wpi-europe.com/pumps/Pneumatic_PicoPumps.html, printed Sep. 18, 2003 (5 pages).

World Precision Instruments, Inc., "Nanoliter 2000," http://www.wpi-europe.com/pumps/Nanoliter_Injector.html, printed Sep. 18, 2003 (3 pages).

World Precision Instruments, Inc., http://www.wpiinc.com/WPI_Web/Pumps/pneumatic_Fig.gif, printed Sep. 30, 2002 (1 page).

World Precision Instruments, Inc., "Pneumatic PicoPumps," httm://www.wpiinc.com/WPI_Web/Microinjection/Pneumatic_PicoPumps.html, printed Sep. 18, 2003 (4 pages).

* cited by examiner

STENT COATING SYSTEM

TECHNICAL FIELD

This invention relates to an apparatus used in the process of coating a stent, and more particularly provides a nozzle for use in drug eluting stent spray coating.

BACKGROUND

Blood vessel occlusions are commonly treated by mechanically enhancing blood flow in the affected vessels, such as by employing a stent. Stents act as scaffolding, functioning to physically hold open and, if desired, to expand the wall of affected vessels. Typically stents are capable of being compressed, so that they can be inserted through small lumens via catheters, and then expanded to a larger diameter once they are at the desired location. Examples in the patent literature disclosing stents include U.S. Pat. No. 4,733,665 issued to Palmaz, U.S. Pat. No. 4,800,882 issued to Gianturco, and U.S. Pat.No. 4,886,062 issued to Wiktor.

Stents are used not only for mechanical intervention but also as vehicles for providing biological therapy. Biological therapy can be achieved by medicating the stents. Medicated stents provide for the local administration of a therapeutic substance at the diseased site. Local delivery of a therapeutic substance is a preferred method of treatment because the substance is concentrated at a specific site and thus smaller total levels of medication can be administered in comparison to systemic dosages that often produce adverse or even toxic side effects for the patient.

One method of medicating a stent involves the use of a polymeric carrier coated onto the surface of the stent. A composition including a solvent, a polymer dissolved in the solvent, and a therapeutic substance dispersed in the blend is applied to the stent by spraying the composition onto the stent. The solvent is allowed to evaporate, leaving on the stent surfaces a coating of the polymer and the therapeutic substance impregnated in the polymer.

However, a shortcoming of the above-described method of medicating a stent is the potential for clogging of a spray nozzle used to the coat the stent. The clogging is caused by accumulation of solid polymer on and around the nozzle tip from which the polymer solution exits. The clogging can lead to a drift in the flow rate, which in turn leads to a variation in total drug content from stent to stent, a variation in the drug release rate from stent to stent, and non-uniform coating of the stents.

Accordingly, a new nozzle for spraying coating is needed to minimize nozzle blockage and the associated variability in the coating behavior.

SUMMARY

In an embodiment of the invention, a stent coating apparatus comprises a solvent pump; a polymer pump; an atomizer and a nozzle assembly. Note that when the polymer pump or a polymer are referred to hereinafter, the polymer typically, but not necessarily, includes solutions of polymer or polymer plus drug in solvent. The solvent pump pumps a solvent from a solvent reservoir. The polymer pump pumps a polymer from a polymer reservoir. The atomizer atomizes the solvent and polymer.

The nozzle assembly comprises a polymer feed conduit, a solvent feed conduit, and an atomizing air conduit. The polymer feed conduit, which is in fluid communication with the polymer reservoir, dispenses the polymer. The solvent feed conduit, which is in fluid communication with the solvent reservoir but not in fluid communication with the polymer conduit, dispenses the solvent. The solvent mixes with the polymer when the polymer and the solvent are dispensed out from the nozzle assembly. The atomizing air conduit, which is in communication with the atomizer but not in fluid communication with the polymer and solvent conduits, uses atomizer air from the atomizer to atomize the dispensed solvent and polymer.

In an embodiment of the invention, the method comprises positioning the nozzle assembly next to a stent; discharging the solvent and polymer so that they mix as the solvent and polymer are discharged; and atomizing the solvent and polymer.

BRIEF DESCRIPTION OF THE DRAWINGS

Non-limiting and non-exhaustive embodiments of the present invention are described with reference to the following figures, wherein like reference numerals refer to like parts throughout the various views unless otherwise specified.

FIG. 2 is a cross section illustrating the nozzle tip of the coating system of FIG. 1 in accordance with an embodiment of the invention;

FIG. 3 is a bottom view of the nozzle tip of the nozzle tip of FIG. 1;

DETAILED DESCRIPTION

Figure 1:
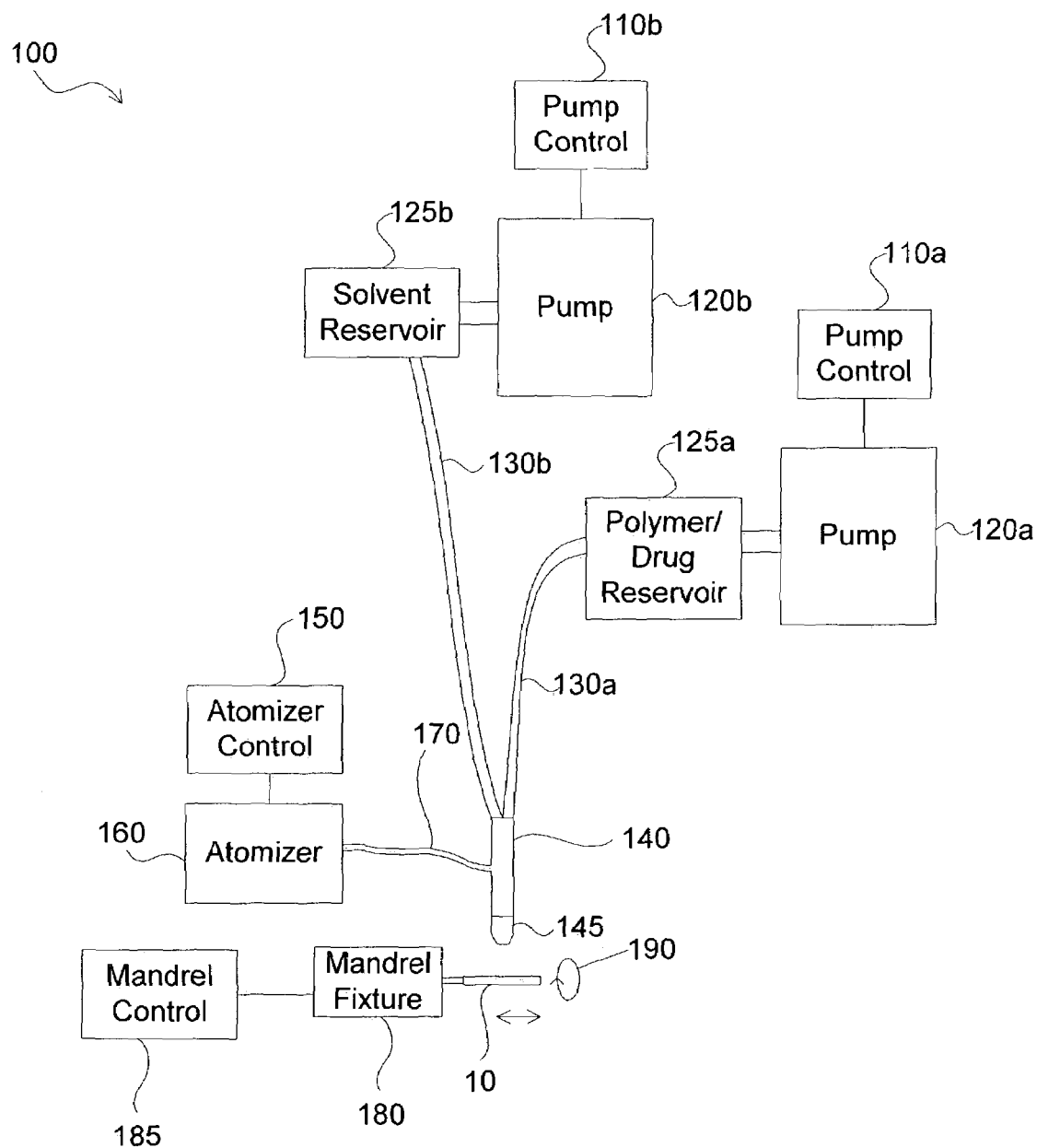
FIG. 1 is a block diagram illustrating a coating system for coating a stent with a composition.

FIG. 1 is a block diagram illustrating a coating system 100 for coating a stent 10 with a composition. The coating system 100 comprises pump controls 110a and 110b; pumps 120a and 120b; a polymer and/or drug reservoir 125a (referred to hereinafter as polymer/drug reservoir 125a), which may optionally include solvent(s) (for placing polymer and/or drug in a liquid composition form); a solvent reservoir 125b; a nozzle assembly 140 having a nozzle tip 145; an atomizer control 150; an atomizer 160; a mandrel fixture 180; and a mandrel fixture control 185. The pump control 110a is communicatively coupled to the pump 120a and controls the amount of polymer and/or drug dispensed by the pump 120a from the polymer/drug reservoir 125a. The pump control 110a may include mechanical and/or electrical control mechanisms. In an embodiment of the invention, the pump control 110a is integrated with the pump 120a. Similarly, the pump control 110b is communicatively coupled to the pump 120b and controls the amount of solvent dispensed by the pump 120b from the solvent reservoir 125b. The pump control 110b may include mechanical and/or electrical control mechanisms. In an embodiment of the invention, the pump control 110b is integrated with the pump 120b. In another embodiment of the invention, the pump controls 110a and 110b are combined into a single unit that controls the pumps 120a and 120b.

The pumps 120a and 120b pump a polymer/drug combination and a solvent from the reservoirs 125a and 125b respectively, for coating the stent 10 in situ, to the nozzle assembly 140 via a tubing 130a and 130b respectively. The pumps 120a and 120b may pump the contents of the reservoirs 125a and 125b at a rate of 0.15 cc/min, for example. In an embodiment of the invention, the pumps 120a and 120b can pump the contents of the reservoirs 125a and 125b, respectively, at different rates. Further, the pump 120b may alone pump solvent so as to clean the nozzle 140. In one embodiment of the invention, the pumps 120a and 120b include a syringe pumps. In another embodiment of the invention, the pumps 120a and 120b include a gear pumps. It will be appreciated that the pumps 120a and 120b can comprise other types of pumps and/or combinations of pumps such as positive displacement pumps, constant displacement pumps or green pumps.

Representative examples of polymers that can be used to coat a stent include ethylene vinyl alcohol copolymer (commonly known by the generic name EVOH or by the trade name EVAL); poly(hydroxyvalerate); poly(L-lactic acid); polycaprolactone; poly(lactide-co-glycolide); poly(glycerol-sebacate); poly(hydroxybutyrate); poly(hydroxybutyrate-co-valerate); polydioxanone; polyorthoester; polyanhydride; poly(glycolic acid); poly(D,L-lactic acid); poly(glycolic acid-co-trimethylene carbonate); polyphosphoester; polyphosphoester urethane; poly(amino acids); cyanoacrylates; poly(trimethylene carbonate); poly(iminocarbonate); copoly (ether esters) (e.g. PEO/PLA); polyalkylene oxalates; polyphosphazenes; biomolecules, such as fibrin, fibrinogen, cellulose, starch, collagen and hyaluronic acid; polyurethanes; silicones; polyesters; polyolefins; polyisobutylene and ethylene-alphaolefin copolymers; acrylic polymers and copolymers; vinyl halide polymers and copolymers, such as polyvinyl chloride; polyvinyl ethers, such as polyvinyl methyl ether; polyvinylidene halides, such as polyvinylidene fluoride, poly(vinylidene fluoride-co-hexafluoropropene), and polyvinylidene chloride; polyacrylonitrile; polyvinyl ketones; polyvinyl aromatics, such as polystyrene; polyvinyl esters, such as polyvinyl acetate; copolymers of vinyl monomers with each other and olefins, such as ethylene-methyl methacrylate copolymers, acrylonitrilestyrene copolymers, ABS resins, and ethylene-vinyl acetate copolymers; polyamides, such as Nylon 66 and polycaprolactam; alkyd resins; polycarbonates; polyoxymethylenes; polyimides; polyethers; epoxy resins; polyurethanes; rayon; rayon-triacetate; cellulose; cellulose acetate; cellulose butyrate; cellulose acetate butyrate; cellophane; cellulose nitrate; cellulose propionate; cellulose ethers; and carboxymethyl cellulose.

"Solvent" is defined as a liquid substance or composition that is compatible with the polymer and/or the therapeutic substance and is capable of dissolving the polymer and/or therapeutic substance at the concentration desired. The solvent in the solvent reservoir 125b could be, in one embodiment, an excellent solvent for the polymer but a poor solvent for the therapeutic substance. Examples of solvents include, but are not limited to, dimethylsulfoxide, chloroform, acetone, water (buffered saline), xylene, methanol, ethanol, 1-propanol, tetrahydrofuran, 1-butanone, dimethylformamide, dimethylacetamide, cyclohexanone, ethyl acetate, methylethylketone, propylene glycol monomethylether, isopropanol, isopropanol admixed with water, N-methyl pyrrolidinone, toluene, and mixtures and combinations thereof.

The therapeutic substance or drug can be for inhibiting the activity of vascular smooth muscle cells. More specifically, the active agent can be aimed at inhibiting 20 abnormal or inappropriate migration and/or proliferation of smooth muscle cells for the inhibition of restenosis. The active agent can also include any substance capable of exerting a therapeutic or prophylactic effect in the practice of the present invention. For example, the agent can be for enhancing wound healing in a vascular site or improving the structural and elastic properties of the vascular site. Examples of agents include antiproliferative substances such as actinomycin D, or derivatives and analogs thereof (manufactured by Sigma-Aldrich 1001 West Saint Paul Avenue, Milwaukee, Wis. 53233; or COSMEGEN available from Merck). Synonyms of actinomycin D include dactinomycin, actinomycin IV, actinomycin $I_1$, actinomycin $X_1$, and actinomycin $C_1$. The active agent can also fall under the genus of antineoplastic, antiinflammatory, antiplatelet, anticoagulant, antifibrin, antithrombin, antimitotic, antibiotic, antiallergic and antioxidant substances. Examples of such antineoplastics and/or antimitotics include paclitaxel (e.g. TAXOL® by Bristol-Myers Squibb Co., Stamford, Conn.), docetaxel (e.g. Taxotere®, from Aventis S.A., Frankfurt, Germany) methotrexate, azathioprine, vincristine, vinblastine, fluorouracil, doxorubicin hydrochloride (e.g. Adriamycino from Pharmacia & Upjohn, Peapack N.J.), and mitomycin (e.g. Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax™ (Biogen, Inc., Cambridge, Mass.). Examples of such cytostatic or antiproliferative agents include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.); calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is pennirolast potassium. Other therapeutic substances or agents which may be appropriate include alpha-interferon, genetically engineered epithelial cells, dexamethasone, and rapamycin.

The atomizer 160 supplies high-pressure air to the nozzle assembly 140 via a tubing 170. This high-pressure air is used to atomize the polymer/drug composition and the solvent dispensed from the nozzle assembly 140 onto the stent 10, as will be discussed in further detail below. The atomizer control 150 is communicatively coupled to the atomizer 160 and controls the pressure of the air dispensed from the atomizer 160 to the nozzle assembly 140. The atomizer control 150 can include electrical mechanisms, mechanical mechanisms, or a combination thereof to control the atomizer 160. In an embodiment of the invention, the atomizer control 150 and the atomizer 160 can be integrated into a single device. In another embodiment of the invention, the atomizer 160 can include an ultrasonic atomizer that uses ultrasound in place of atomizing air to atomize the polymer/drug composition and the solvent.

The mandrel fixture 180 supports the stent 10 during a coating application process. In addition, the mandrel fixture 180 can include an engine so as to provide rotational motion about the longitudinal axis of the stent 10, as depicted by the arrow 190, during the coating process. Another motor can also be provided for moving the stent 10 in a linear direction, back and forth. The mandrel control 185 is communicatively coupled to the mandrel fixture 180 and controls movement of the stent 10. The type of stent that can be crimped on the mandrel fixture 180 is not of critical significance. The term stent is broadly intended to include self- and balloon-type expandable stents as well as stent-grafts. It will be appreciated by one of ordinary skill in the art that other implantable devices can be used in place of stents.

The nozzle assembly 140, as will be discussed in further detail in conjunction with FIGS. 2-5, receives the polymer/drug solution (i.e., with or without solvent(s)) via the tubing 130a and the solvent via the tubing 130b. In addition, the nozzle assembly 140 receives high-pressure air from the atomizer 160. During a stent coating application process, the nozzle assembly 140 dispenses, via the nozzle tip 145, the polymer/drug solution and the solvent, which combines in situ, onto the stent 10. In other words, a pure solvent (e.g., about 90% to about 100% polymer and drug free) blends with the coating composition (i.e., polymer and/or drug composition with or without a solvent) out from the nozzle tip 145 before contacting the stent 10. It should be noted, therefore, that the coating composition should be formulated to compensate for the blending of the pure solvent with the composition. During the dispensing, high-pressure air from the atomizer 160 atomizes the combined polymer/drug solution and solvent, leading to a more uniform distribution on the stent 10.

It will be appreciated that the multiple control devices, i.e., the pump controls 110a and 110b, atomizer control 150, and mandrel control 185 can be combined into a single control device to simplify setting parameters for an operator.

Figures 2, 3:
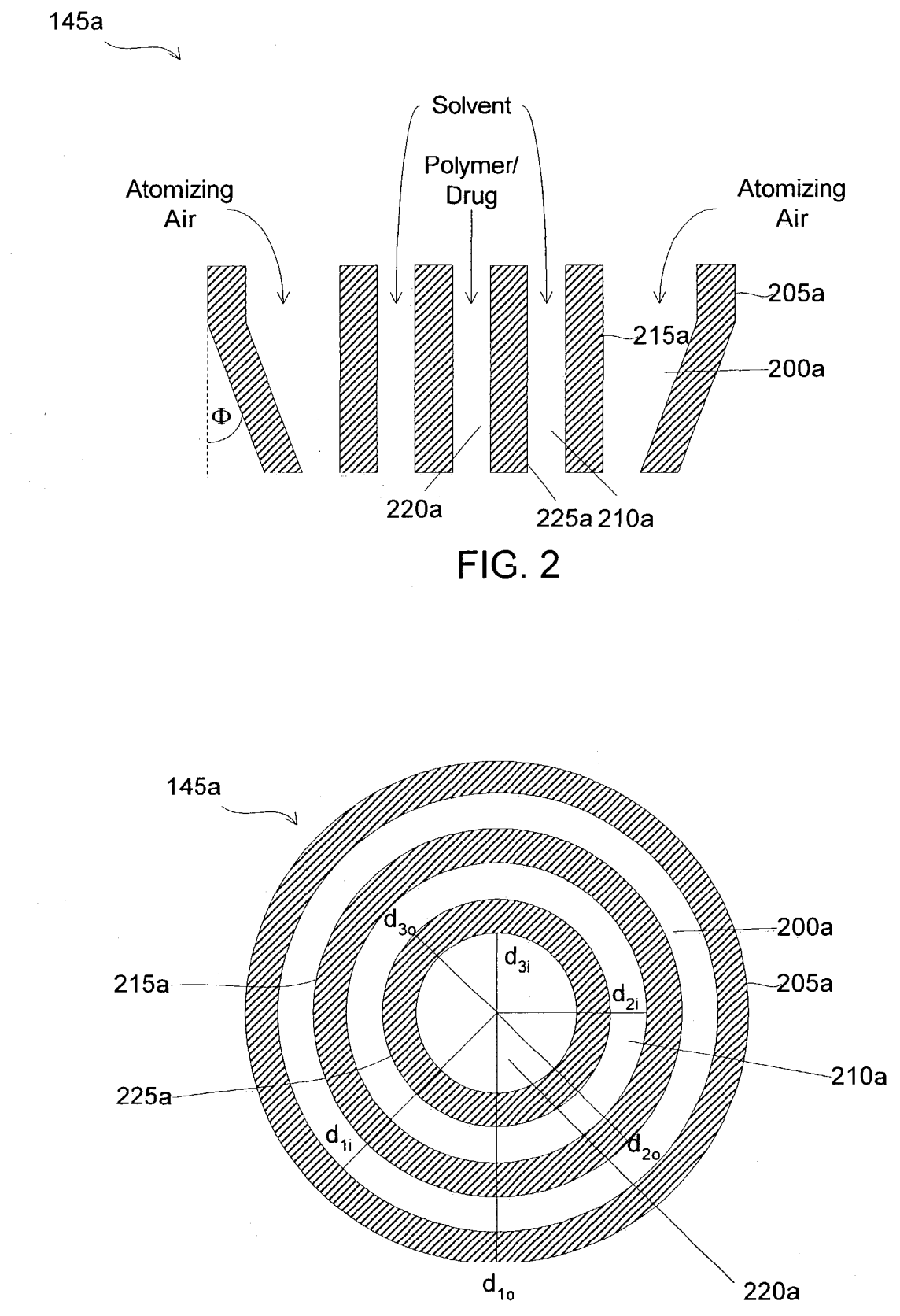

FIG. 2 is a cross section illustrating a nozzle tip 145a of the coating system 100 (FIG. 1) in accordance with an embodiment of the invention. The nozzle tip 145a includes an atomizing air conduit 200a; a solvent feed conduit 210a; and a polymer/drug feed conduit 220a. In an embodiment of the invention, the air conduit 200a, the solvent feed conduit 210a, and the polymer/drug feed conduit 220a are concentrically positioned tubes, hypotubes, or syringes that run parallel to each other. The atomizing air conduit 200a is in communication with the atomizer 160 via the tubing 170 from which it receives atomizing air. The air conduit 200a circumscribes the solvent feed conduit 210a, which circumscribes the polymer/drug feed conduit 220a, and expels the atomizing air during a coating process so as to atomize the solvent and the polymer/drug expelled from the solvent feed conduit 210a and polymer/drug feed conduit 220a respectively. It will be appreciated by one of ordinary skill in the art that the polymer/drug feed conduit 220a can circumscribe the solvent feed conduit 210a instead of vice versa.

A tube 205a of the air conduit 200a has an inner diameter $d_{1i}$ of about 0.0225 to about 0.45 inches and an outer diameter $d_{1o}$ of about 0.0275 to about 0.50 inches (at the segment of the tube that is not bent). The tube 205a of the air conduit 200a is bent inwards to form an acute angle Φ of about 0 to about 60 degrees relative to a tube 215a of the solvent feed conduit 210a so as to bias the velocity of the exiting atomizing air towards the dispensed solvent and polymer/drug solution.

Figure 6:
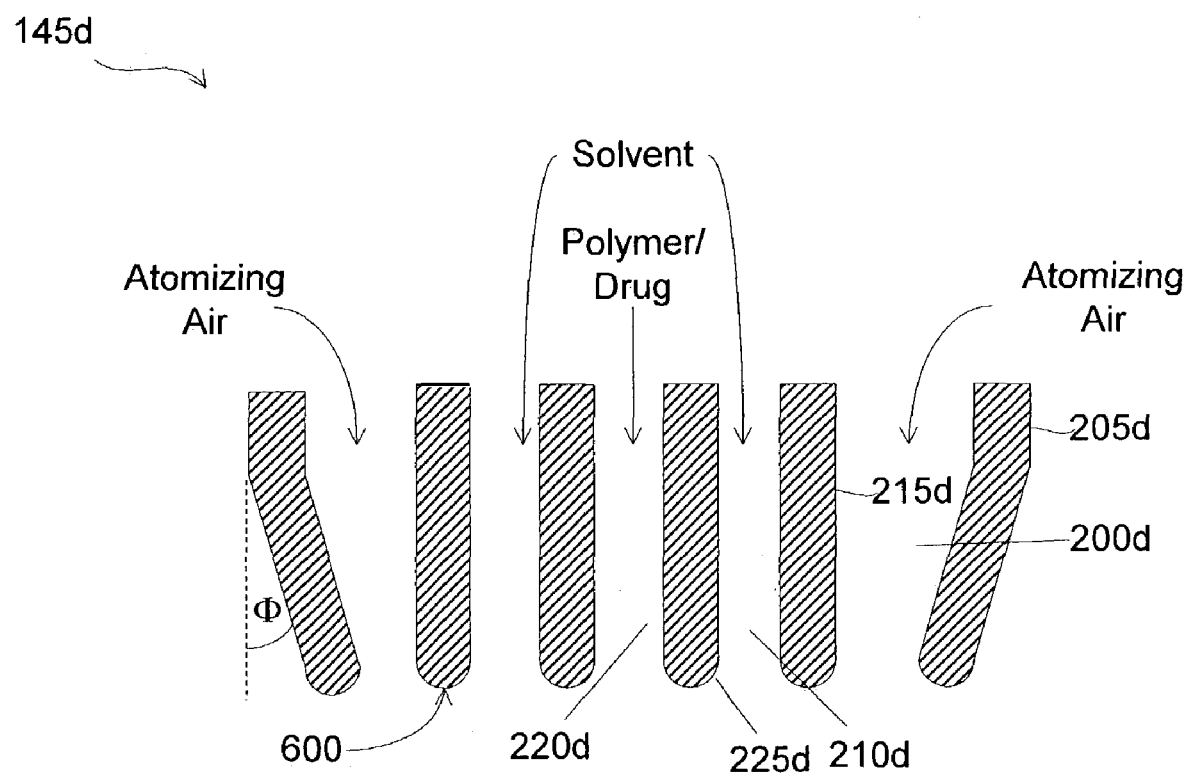
FIG. 6 is a cross section illustrating a nozzle tip according to a fourth embodiment of the invention.

The tube 215a of the solvent feed conduit 210a has an inner diameter $d_{2o}$ of about 0.0175 to about 0.25 inches and an outer diameter $d_{2o}$ of about 0.0125 to about 0.20 inches and dispenses pure solvent. The solvent acts to prevent clogging of the polymer/drug feed conduit 220a by preventing accumulation of polymer and/or drugs on a tube 225a of the polymer/drug feed conduit 220a. The solvent mixes in situ with the dispensed polymer/drug when it is ejected out from the nozzle tip 145a. Since only a pure solvent is ejected from the solvent feed conduit 210a, the size of this conduit can be smaller than the size of the polymer/drug conduit 220a, which should be sized to allow for the ejection of a more viscous polymer and/or drug composition. In an embodiment of the invention, the tube 225a, as well as the tubes 205a and 215a, can each have an arcuate end, such as end 600 as shown in FIG. 6, to further prevent accumulation of polymer that may cause blockage. In addition, the tubes 205a, 215a, and 225a can be made of or coated with a non-stick material (e.g., TEFLON) to prevent accumulation of the polymer, which can lead to blockage.

The polymer/drug feed conduit 220a dispenses a polymer and/or drug from the polymer/drug reservoir 125a received via the tubing 130a. In an embodiment of the invention, the tube 225a of the polymer/drug feed conduit 220a has an inner diameter $d_{3i}$ of about 0.0025 to about 0.05 inches and an outer diameter $d_{3o}$ of about 0.0075 to about 0.10 inches.

FIG. 3 is a bottom view of the nozzle tip of the nozzle tip 145a. The polymer/drug feed conduit 220a is centered with the nozzle tip 145a. The solvent feed conduit 210a circumscribes the polymer/drug feed conduit 220a. The atomizing air conduit 200a circumscribes the solvent feed conduit 210a.

Figure 4:
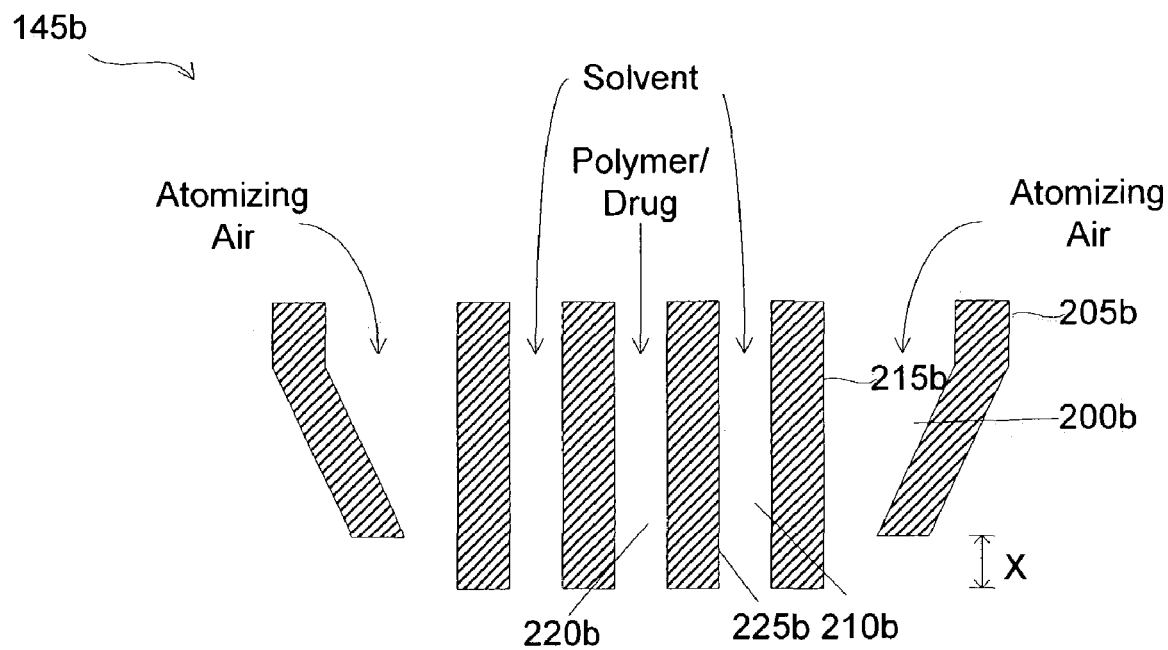
FIG. 4 is a cross section illustrating a nozzle tip according to a second embodiment of the invention.

FIG. 4 is a cross section illustrating a nozzle tip 145b according to another embodiment of the invention. The nozzle tip 145b is substantially similar to the nozzle tip 145a and includes the same components. However, the tube 205b of the air conduit 200b does not extend to the same length as the tube 215b of the solvent feed conduit 210b, i.e., the air conduit tube 205b is shorter than the solvent feed conduit tube 215b by a distance X of, for example, up to about 0.2 inches. This nozzle tip 145b geometry substantially prevents any polymer clumping within the air conduit 200b since the tubes 215b and 225b extend out from the tube 205b.

Figure 5:
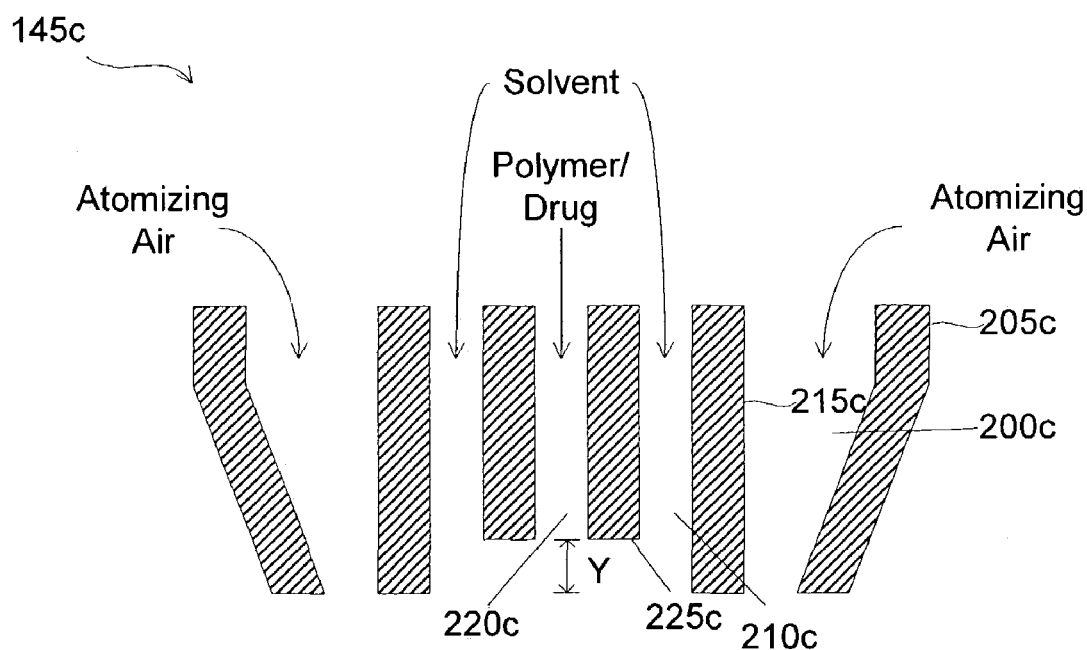
FIG. 5 is cross section illustrating a nozzle tip according to a third embodiment of the invention.

FIG. 5 is cross section illustrating a nozzle tip 145c according to another embodiment of the invention. The nozzle tip 145c is substantially similar to the nozzle tip 145a and includes the same components. However, the polymer/drug feed conduit tube 225c is shorter than the solvent feed conduit tube 215c that circumscribes it, i.e., the polymer/drug feed conduit 220c is recessed within the solvent feed conduit 210c by a distance Y of, for example, up to about 0.2 inches. This nozzle tip 145c geometry substantially prevents any polymer clumping within the air conduit 200c and also ensures that the bottom of the tube 225c is swept clean with solvent from the solvent feed conduit 210c. It should also be noted that the tube 215c can also be recessed in the same extent as the tube 225c or be positioned such that the bottom of the tube 215c is between the bottom of the tubes 205c and 225c.

FIG. 6 is cross section illustrating a nozzle tip 145d according to a fourth embodiment of the invention. The nozzle tip 145d is substantially similar to the nozzle tip 145a and includes the same components. However, each of the tubes 205d, 215d, and 225d have arcuate ends, such as arcuate end 600. The arcuate ends of the tubes 205d, 215d, and 225d enable the solvent to contact more of the tubes' surface area, thereby prevent accumulation of the polymer on the tubes 205d, 215d, and 225d, which may lead to clogging of the nozzle tip 145d.

While particular embodiments of the present invention have been shown and described, it will be obvious to those skilled in the art that changes and modifications can be made without departing from this invention in its broader aspects. For example, the nozzle tip 145 can use internal mixing in place of external mixing. Therefore, the appended claims are to encompass within their scope all such changes and modifications as fall within the true spirit and scope of this invention.

What is claimed is:

1. A stent coating system, comprising:
   a solvent pump that pumps a solvent contained in a solvent reservoir;
   a polymer pump that pumps a polymer contained in a polymer reservoir;
   an atomizer that atomizes the solvent and polymer; and
   a nozzle assembly having
      a polymer feed conduit, in fluid communication with the polymer reservoir, that dispenses the polymer,
      a solvent feed conduit, in fluid communication with the solvent reservoir, that is not in fluid communication with the polymer feed conduit and dispenses the solvent, wherein the solvent mixes with the polymer only after the polymer and solvent are dispensed out from the nozzle assembly, and
      an atomizing air conduit, in communication with the atomizer, that is not in fluid communication with the polymer feed conduit and the solvent feed conduit and that uses atomizer air from the atomizer to atomize the solvent and polymer that are dispensed out from the nozzle assembly;
   wherein the polymer reservoir holds a polymer and drug mixture.

2. The system of claim 1, further comprising a stent mandrel fixture capable of securely supporting a stent during a coating process.

3. The system of claim 2, wherein the stent mandrel fixture is further capable of rotating or translating the stent during a coating process.

4. The system of claim 1, wherein the nozzle assembly enables external atomization of the solvent and polymer.

5. The system of claim 1, wherein the solvent of the solvent reservoir is a better solvent for the polymer than for the drug.

6. The system of claim 1, wherein an outlet section of the atomizing air conduit is angled relative to the polymer and solvent feed conduits.

7. The system of claim 1, wherein the solvent or polymer feed conduit extends out from the atomizing air conduit.

8. The system of claim 1, wherein the polymer feed conduit is recessed with respect to the solvent feed conduit.

9. A stent coating system, comprising:
   a solvent pump that pumps a solvent contained in a solvent reservoir;
   a polymer pump that pumps a polymer contained in a polymer reservoir;
   an atomizer that atomizes the solvent and polymer; and
   a nozzle assembly having
      a polymer feed conduit, in fluid communication with the polymer reservoir, that dispenses the polymer,
      a solvent feed conduit, in fluid communication with the solvent reservoir, that is not in fluid communication with the polymer feed conduit and dispenses the solvent, wherein the solvent mixes with the polymer only after the polymer and solvent are dispensed out from the nozzle assembly, and
      an atomizing air conduit, in communication with the atomizer, that is not in fluid communication with the polymer feed conduit and the solvent feed conduit and that uses atomizer air from the atomizer to atomize the solvent and polymer that are dispensed out from the nozzle assembly, wherein the polymer feed conduit is positioned within the solvent feed conduit such that the solvent feed conduit circumscribes the polymer feed conduit, and wherein the polymer reservoir holds a polymer and drug mixture.

10. A stent coating system, comprising:
    a solvent contained in a solvent reservoir;
    a polymer contained in a polymer reservoir; and
    a nozzle assembly having
       a polymer feed conduit that dispenses the polymer contained in the polymer reservoir,
       a solvent feed conduit that dispenses the solvent contained in the solvent reservoir, wherein the solvent and polymer mix only after the polymer and solvent have been dispensed out from the nozzle assembly, and
       an atomizing air conduit that dispenses air to atomize the solvent and polymer only outside of the nozzle assembly after the solvent and polymer have been dispensed out from the nozzle assembly.

11. The system of claim 10, wherein the polymer feed conduit is positioned within the solvent feed conduit such that the solvent feed conduit circumscribes the polymer feed conduit.

12. The system of claim 10, wherein the solvent or polymer feed conduit extends out from the atomizing air conduit.

13. The system of claim 10, wherein the polymer feed conduit is recessed with respect to the solvent feed conduit.

* * * * *